United States Patent [19]

Bannon

[11] Patent Number: 4,755,207

[45] Date of Patent: Jul. 5, 1988

[54] SYNERGISTIC MYCOHERBICIDAL COMPOSITIONS

[75] Inventor: James S. Bannon, Ruston, La.

[73] Assignee: Mycogen Corporation, San Diego, Calif.

[21] Appl. No.: 890,257

[22] Filed: Jul. 28, 1986

[51] Int. Cl.$^4$ ............................................. A01N 63/04
[52] U.S. Cl. .................................... 71/79; 71/DIG. 1
[58] Field of Search ............................. 71/79, DIG. 1

[56] References Cited

U.S. PATENT DOCUMENTS 4,263,036  4/1981  Charudattan ........................... 71/79
4,390,360  6/1983  Walker .................................... 71/79

OTHER PUBLICATIONS

Dhingra, O. D. and Sinclair, J. B. (1985) in Basic Plant Pathology Methods, CRC Press, Inc., Boca Raton, Fla., p. 137.
Bushnell, W. R. and Rowell, J. B. (1967) Plant Dis. Rep. 51:447 "Fluorochemical Liquid as a Carrier for Spores of *Erysiphe graminis Puccini graminis*".
Hawker, L. E. and Madelin, M. F. (1976), "The Dormant Spore" in the Fungal Spore, Form and Function, D. J. Weber and W. M. Hess, eds. John Wiley and Sons, N.Y., pp. 46-48.
Fisher, D. J., Holloway, P. J. and Richmond, D. V. (1972) "Fatty Acid and Hydrocarbon Constituents of the Surface and Wall Lipids of Some Fungal Spores", J. Gen. Microbiol. 72:71-78.

*Primary Examiner*—Catherine L. Mills
*Attorney, Agent, or Firm*—Roman Saliwanchik; David R. Saliwanchik

[57] ABSTRACT

The synergistic herbicidal compositions of the invention comprise a non-phytotoxic crop oil, a surfactant, and a hydrophobic mycoherbicide spore. This composition is useful to control undesirable plants, generally referred to as weeds, by application of the composition with standard agricultural spray equipment to the undesirable plant. Exemplified herein is the application of *Alternaria cassiae* spores in mixture with well-known non-phytotoxic crop oil:surfactant products to the well-known weed, sicklepod. The results, as shown in Table 1, are dramatically synergistic and, thus, presage a high degree of practical utility for the subject invention in weed control.

8 Claims, No Drawings

SYNERGISTIC MYCOHERBICIDAL COMPOSITIONS

BACKGROUND OF THE INVENTION

Mycoherbicides are delivered to the weed target species as spores, mycelia, or other living propagules of the fungus. Spores of various fungi may be classified as hydrophobic or hydrophilic, and this property could determine the nature of various mycoherbicide formulations. As such, a hydrophobic spore, e.g., *Alternaria cassiae*, requires the addition of a surfactant to an aqueous spore suspension to facilitate dispersion. See U.S. Pat. No. 4,390,360.

In addition to being utilized in an actual mycoherbicidal concentrate, surfactants are also used in spray solutions to facilitate mycoherbicide penetration into the plant. The addition of a surfactant to either the concentrate of the actual spray solution can enhance or retard herbicidal efficacy, or it may have no effect. The effect of surfactants on mycoherbicidal efficacy is complicated by the fact that the surfactant may also affect the infection, virulence, germination or other property of the living mycoherbicidal propagule.

Regardless of the type of mycoherbicidal concentrate formulation, a wetting agent will be used in the spray solution of postemergence mycoherbicides to achieve even distribution of the mycoherbicide over the leaf surface. Wetting agents often comprise from 0.02% to 2% v/v of the aqueous spray solution.

It has been documented that spore suspensions in sterile water, fluorochemicals, oil or talc can be atomized onto leaf surfaces to inoculate plants (Dhingra, O. D. and Sinclair, J. B. [1985] Basic Plant Pathology Methods, CRC Press, Inc. Boca Raton, FL, p. 137). The use of non-phytotoxic oils as a suspending medium is also documented (Dhingra and Sinclair); however, some conidia may lose infectivity when suspended in oil (Bushnell, W. R. and Rowell, J. B. [1967] Plant Dis. Rep. 51: 447). It has been recently stated by Dhingra and Sinclair that oils maintain a uniform suspension of spores more easily than does water, and no surfactant needs to be added.

The wettability of the spore surface has been described as being an extremely variable physical property (Hawker, L. E. and Madelin, M. F. (1976) in The Fungal Spore, Form and Function, D. J. Weber and W. M. Hess, eds. John Wiley and Sons, New York, pp. 1–70), and variation has been observed among species of the same genus. The presence of surface lipids in spores of *Alternaria tenuis*, *Botrytis fabae*, and *Neurospora crassa* probably contributes to their hydrophobic nature, although hydrophobicity is also noted in Penicillium sp., Aspergillus sp. and Erisyphe sp. which lack surface lipids. *Verticillium albo-atrum* and *Nectria galligena* also lack surface lipids (Fisher, D. J., Holloway, P. J. and Richmond, D. V. [1972] J. Gen. Microbiol. 72: 71–78) but they are hydrophilic. Thus, hydrophobicity/hydrophilicity of the spore surface is not a predictable variable. Yet, it is very important to understand this property to optimize inoculation of a plant with a mycoherbicide. For example, a hydrophilic, water-dispersed spore is not very easily dispersed in an oil. Conversely, a hydrophobic spore would not be very easily dispersed in water without the aid of a surfactant.

BRIEF SUMMARY OF THE INVENTION

The subject invention concerns the unexpected discovery that certain mixtures of non-phytotoxic crop oils, surfactants, and hydrophobic mycoherbicide spores produce a synergistic effect against target weeds. For example, the use of non-phytotoxic crop oils and a surfactant with *Alternaria cassiae* spores extends the range of environmental conditions in which the mycoherbicide will function against the weed, sicklepod (*Cassia obtusifolia* L.). See Table 1. The mycoherbicidal composition of the subject invention can be applied via standard spray equipment to the target weed.

This synergistic results in weed control is unexpected in view of prior art teaching, as discussed above. For example, the recent publication by Dhingra and Sinclair (1985, Basic Plant Pathology Methods, CRC Press, Inc., Boca Raton, FL, Chapter 5) clearly leads a person skilled in the art away from even trying a mycoherbicidal composition comprising a mycoherbicide spore, a non-phytotoxic oil and a surfactant. That such a composition, as disclosed herein, gives a synergistic result in weed control is surprising and unpredictable from prior art teachings.

DETAILED DESCRIPTION OF THE INVENTION

Upon applying a mycoherbicidal spray composition comprising a hydrophobic mycoherbicide spore, a surfactant, and a non-phytotoxic crop oil to a target weed, there is obtained a synergistic control of the target weed upon germination of the mycoherbicide spore and subsequent disease development.

This novel mycoherbicidal composition can be used to control target weeds in fields planted with desired crops, along roadways, river banks, lake shores, in recreational areas, and the like.

The subject invention can be used with any mycoherbicide spore exhibiting hydrophobic properties. As discussed above, such mycoherbicides can be present in various genera of fungi. The hydrophobic property of a particular mycoherbicide spore can be readily determined by a person skilled in the art using simple tests such as immersing mycoherbicide spores in water and determining if they float at the surface of the water. Those that stay at the surface would be hydrophobic, whereas those that sink after a period of time, e.g., 10 min, are hydrophilic.

The use of a particular mycoherbicide will be as the mycoherbicide is normally used in spray form against weeds it is active against. For example, the *A. cassiae* exemplified herein is used to control the weed sicklepod.

The concentration of spores used is what is normally used for the particular mycoherbicide spore. Generally, a spore concentration of from about $1 \times 10^4$ to about $1 \times 10^6$ spores/ml can be used for the various mycoherbicides.

Spores of one hydrophobic mycoherbicide can be combined with those of another hydrophobic mycoherbicide to enlarge the scope of control of undesirable vegetation. For example, *A. cassiae* spores can be combined with another hydrophobic mycoherbicide spore in the novel composition of the invention to enlarge the scope of control of undesirable vegetation.

Spores of hydrophobic mycoherbicides can be combined with various chemical additives, particularly chemical herbicides, to increase weed control. These additives would be expected to broaden the spectrum of activity so that additional species of weeds can be controlled. Application rates of these chemicals would be expected to be less than or equal to the rates recommended for conventional use.

Examples of these chemicals include but are not limited to the following:

| Trade Name[1] | Chemical Name | Common Name |
|---|---|---|
| ALANAP (B) | 2-[(1-naphthalenylamino)carbonyl] benzoic acid | naptalam |
| BASAGRAN (B) | Sodium salt of (3-isopropyl-1 H—2,1,3-bentzothiadiazin-4 (3H)—one 2,2-dioxide) | bentazon sodium salt |
| BASTA (B & G) | Ammonium-DL-homoalanin-4-yl (methyl) phosphinate | glufosinate ammonium |
| BLAZER (B & G) | Sodium 5-[2-chloro-4-trifluoro methyl)phenoxy]-2-nitrobenzoate | acifluorfen sodium salt |
| BUTYRAC 200 (B) | 4-(2,4-Dichlorophenoxy)butyric acid | 2,4-DB |
| COBRA (B) | 1-(carboethoxy)ethyl 5-[2-chloro-4-(trifluoromethyl)phenoxy]-2-nitrobenzoate | lactofen |
| DOWPON (G) | 2,2'-dichloropropionic acid | dalapon |
| FUSILADE (G) | Butyl(R—S)—2-[4-[[5-(trifluoro-methyl)-2-pyridinyl]oxy]phenoxy] propanoate | fluazifop |
| HOELON (G) | Methyl 2-[4-(2,4-dichlorophenoxy) phenoxy]propanoate | diclofop methyl |
| PRE-MERGE 3 (B & G) | Dinoseb(2-sec-butyl-4,6-dinitro-phenol) as the alkanolamine salts | dinoseb |
| ROUNDUP (B & G) | Isopropylamine salt of N—(phosphonomethyl)glycine | glyphosate |
| SCEPTER (B) | Ammonium salt of 2-[4,5-Dihydro-4-methyl ethyl)-5-oxo-1H—imidazol-2-yl]-3-quinoline carboxylic acid | imazaquin |
| CLASSIC | 2-(([(4-chloro-6-methox-pyrimidine-2-yl)amino carbonyl] amino sulfonyl))benzoic acid ethyl ester | DPX-F6025 |
| DUAL 8E | 2-chloro-N—(2-ethyl-6-methyl-phenyl)-N—(2-methoxy-1-methyl-ethyl)acetamide | metolachlor |
| POAST | 2-[1-(ethoxyimino)butyl]-5[2-(ethylthio)propyl]-3-hydroxy-2-cyclohexen-1-one | sethoxydim |
| SENCOR | 4-Amino-6-(1,1-dimethylethyl)-3-(methylthio)-1,2,4,-triazin-5(4H)—one | metribuzin |
| LOROX, LINEX | 3-(3,4-dichlorophenyl)-1-methoxy-1-methylurea | linuron |
| KARMEX | 3-(3,4-dichlorophenyl)-1,1-dimethylurea | diuron |
| SURFLAN | 3,5-Dinitro-$N^4N^4$—dipropyl-sulfanilamide | oryzalin |
| B-NINE | Daminozide butanedioic acid mono(2,2-dimethylhydrazide) | Alar |
| DROPP | N—phenyl-N'—1,2,3-thiadiazol-5-yl urea | thidiazuron |
| EMBARK | Diethanolamine salt of (N—[2,4-dimethyl-5-[[(trifluoromethyl)-sulfonyl]amino]phenyl]acetamide | mefluidide |
| STIK | 1-Naphthaleneacetic acid | NAA |

[1]The notation in parentheses indicates the activity of the herbicide (B = broadleaf control, G = grass control, and B & G = broadleaf and grass control.

The surfactant used in the invention can be a wetting dispersing or emulsifying agent which will assist dispersion of the effective composition. The surfactant can include such anionic, cationic and nonionic agents as have heretofore been generally employed in plant control compositions of similar type. Suitable surfactants are set forth, for example, in "Detergents and Emulsifiers" 1971 Annual by John W. McCutcheon, Inc.

In general, 1–10% by weight of the surfactants can be used and ordinarily the amount of surfactant will range from 1–5% but may even be less than 1% by weight.

Additional surfactants can be added to increase the ratio of surfactants:active ingredients up to as high as 5:1 by weight. When used at higher ratios, it is preferred that the surfactant be present in the range of one-fifth to five parts surfactant for each one part of active agent.

Non-phytotoxic crop oils, as used herein, are once refined vegetable oils obtained from various crops or highly refined paraffinic material. The oils are not toxic to target weeds. Examples of such oils are as follows:

1. SOY-DEX TM (Helena Chemical Co. Memphis, TN), a vegetable oil surfactant containing vegetable oil and a non-ionic blend of alkoxylated alkyl-phenols and fatty acids
2. AGRI-DEX TM (Helena Chemical Co.), a non-ionic spray adjuvant containing paraffin base petroleum oil, polyol fatty esters and poly-ethoxylated derivatives thereof.
3. SUN SPRAY TM (Sun Refining & Marketing Co., Marcus Hook, PA), a 100% light paraffinic distillate
4. Canola oil
5. Soybean oil
6. Cottonseed oil
7. Peanut oil
8. Corn oil
9. Coconut oil
10. Castor oil
11. Esters of compounds 4–10 (alkyl 1–4 C)
12. Emulsified oils of compounds 3–11, e.g., oil + 1–20% emulsifier
13. Blends of compounds 1–12

Following is an example which illustrates the process of the invention, including the best mode. This example should not be construed as limiting. All solvent mixture proportions are by volume unless otherwise noted.

EXAMPLE 1

The field experiment reported in Table 1 was applied with a $CO_2$ backpack research sprayer in 36 gal of diluent per acre. Tap water was utilized as the diluent containing the indicated mixtures in the concentrations shown in Table 1. Temperature was 90 F. at the time of application and the relative humidity was 90%. Windy, dry conditions persisted for 24 hr after application and no dew formation was observed. Because of low moisture, irrigation (0.25") was applied 24 hr after treatments were applied.

TABLE 1

Effect of Various Surfactants and Non-Phytotoxic Crop Oils on Mycoherbicide Efficacy of *Alternaria cassiae* on Sicklepod

| Treatment | Spore Rate, lb/Acre | % Growth Inhibition | | | Visual Observation[1,2] | Standard Deviation |
|---|---|---|---|---|---|---|
| | | Rep. I | Rep. II | Rep. III | Average | |
| *X-77 TM, 0.25% v/v | 1.0 | 25 | 35 | 30 | 30 | 5.0 |
| *X-77 TM, 0.25% v/v | 0.5 | 20 | 30 | 20 | 23 | 5.7 |
| *X-77 TM, 0.25% v/v | 0.25 | 5 | 5 | 20 | 10 | 8.6 |

TABLE 1-continued

Effect of Various Surfactants and Non-Phytotoxic Crop Oils on Mycoherbicide Efficacy of *Alternaria cassiae* on Sicklepod

| Treatment | Spore Rate, lb/Acre | % Growth Inhibition Rep. I | % Growth Inhibition Rep. II | Visual Observation[1,2] Rep. III | Visual Observation[1,2] Average | Standard Deviation |
|---|---|---|---|---|---|---|
| AGRI-DEX TM, 1.0% v/v | 1.0 | 60 | 80 | 85 | 75 | 13.2 |
| AGRI-DEX TM, 1.0% v/v | 0.5 | 35 | 55 | 50 | 47 | 10.4 |
| AGRI-DEX TM, 1.0% v/v | 0.25 | 25 | 25 | 25 | 25 | 0 |
| SOY-DEX TM, 1.0% v/v | 1.0 | 75 | 85 | 90 | 83 | 7.6 |
| SOY-DEX TM, 1.0% v/v | 0.5 | 45 | 70 | 45 | 53 | 14.4 |
| SOY-DEX TM, 1.0% v/v | 0.25 | 25 | 35 | 25 | 28 | 5.7 |
| *STEROX NJ TM, 0.02% v/v | 1.0 | 25 | 35 | 45 | 35 | 10.0 |
| *STEROX NJ TM, 0.02% v/v | 0.5 | 20 | 10 | 20 | 17 | 5.7 |
| *STEROX NJ TM, 0.02% v/v | 0.25 | 10 | 25 | 5 | 13 | 10.4 |
| *TRITON AG-98 TM, 0.25% v/v | 1.0 | 20 | 30 | 30 | 27 | 5.7 |
| *TRITON AG-98 TM, 0.25% v/v | 0.5 | 5 | 15 | 15 | 12 | 5.7 |
| *TRITON AG-98 TM, 0.25% v/v | 0.25 | 5 | 10 | 5 | 7 | 2.8 |
| Control (Untreated) | | 0 | 0 | 0 | 0 | 0 |

[1]Observations made 2 wk after initial treatment.
[2]No dew formation for 24 hours after application.
*Surfactants available as follows:
X-77 TM from Ortho Chemical, Richmond, CA
STEROX NJ TM from Monsanto, St. Louis, MO
TRITON AG-98 TM from Rohm and Haas, Philadelphia, PA

I claim:

1. A process for controlling sicklepod which comprises applying to sicklepod aqueous composition comprising an emulsifiable crop oil consisting of a non-phytotoxic crop oil, and an emulsifier, and *Alternaria cassiae* spores.

2. A process, according to claim 1, wherein the non-phytotoxic crop oil of the composition used in said process is selected from the group consisting of, canola oil, soybean oil, cottonseed oil, peanut oil, corn oil, coconut oil, and castor oil.

3. A process, according to claim 2, wherein the non-phytotoxic crop oil of the composition used in said process is comprised of the lower alkyl esters of said non-phytotoxic crop oils.

4. A process, according to claim 2, wherein the non-phytotoxic crop oil of the composition used in said process is comprised of (a) emulsified oils of said non-phytotoxic crop oils, or
(b) emulsified oils of lower alkyl esters of said non-phytotoxic crop oils.

5. A process, according to claim 2, wherein the non-phytotoxic crop oil of the composition used in said process is comprised of (a) blends of said non-phytotoxic crop oils, or
(b) blends of lower alkyl esters of said non-phytotoxic crop oils, or
(c) blends of emulsified oils of said non-phytotoxic crop oils, or
(d) blends of emulsified oils of lower alkyl esters of said non-phytotoxic crop oils, or
(e) blends of (a), (b), (c), and (d).

6. A process, according to claim 1, for controlling the undesirable plant sicklepod which comprises applying to sicklepod a mixture comprising AGRI-DEX TM and spores of *Alternaria cassiae*.

7. A process, according to claim 1, for controlling the undesirable plant sicklepod which comprises applying to sicklepod a mixture comprising SOY-DEX TM and spores of *Alternaria cassiae*.

8. A process, according to claim 1, wherein the emulsifiable crop oil is selected from the group consisting of SOY-DEX TM, AGRI-DEX TM, and SUN SPRAY TM.

* * * * *